United States Patent [19]

Furukawa et al.

[11] Patent Number: 5,780,650
[45] Date of Patent: Jul. 14, 1998

[54] PROCESS FOR PREPARATION OF 1,4-BENZODIOXANE DERIVATIVE

[75] Inventors: Yoshiro Furukawa, Osaka; Kazuhiro Kitaori; Keishi Takenaka, both of Hyogo, all of Japan

[73] Assignee: Daiso Co., Ltd., Osaka, Japan

[21] Appl. No.: 913,882

[22] PCT Filed: Mar. 21, 1996

[86] PCT No.: PCT/JP96/00727

§ 371 Date: Sep. 24, 1997

§ 102(e) Date: Sep. 24, 1997

[87] PCT Pub. No.: WO96/30360

PCT Pub. Date: Mar. 10, 1996

[30] Foreign Application Priority Data

Mar. 24, 1995 [JP] Japan .................................. 7-066270
Feb. 27, 1996 [JP] Japan .................................. 8-039458

[51] Int. Cl.⁶ .................... C07D 493/00; C07D 319/14
[52] U.S. Cl. ........................ 549/361; 549/362; 549/366
[58] Field of Search ............................. 549/361, 362, 549/366

[56] References Cited

PUBLICATIONS

Delgado, A. et al 'Short and enantioselective synthesis of (R)- and (S)-2-hydroxymethyl-1,4-benzodioxan' Tetrahedron Letters, vol. 29, No. 30 pp. 3671–3674 1988.

JP-6-9613A Benzodioxane Derivative Jan. 1994 Abstract.

Primary Examiner—Amelia Owens
Attorney, Agent, or Firm—Jacobson, Price, Holman & Stern, PLLC

[57] ABSTRACT

A novel process for preparing a 1,4 benzodioxane derivative shown by the formula (1) which is a useful intermediate of circulatory drugs and drugs for psychoneurosis, characterized in sulfonating a phenoxypropanediol with a sulfonyl halide, eliminating the protective group, and then cyclizing the sulfonated compound by treating with a base followed by, if necessary, further sulfonation.

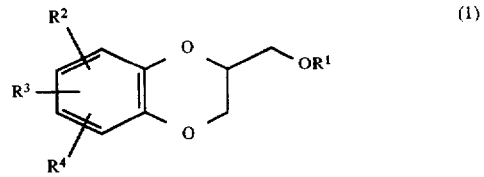

(1)

In the above formula, $R^1$ is H, $RSO_2$, R is alkyl, phenyl which may be substituted with alkyl, $R^2$, $R^3$, $R^4$ are H, halogen, OH, nitro, cyano, formyl, COOH, alkoxycarbonyloxy, alkyl, alkoxy, haloalkyl, N,N-dialkylamino, alkylcarbonyl, alkoxycarbonyl, phenyl which may be substituted by alkyl, etc.22

8 Claims, No Drawings

PROCESS FOR PREPARATION OF 1,4-BENZODIOXANE DERIVATIVE

FIELD OF ART

The present invention relates to a process for the preparation of a 1,4-benzodioxane derivative useful for the intermediate of circulatory drugs and drugs for psychoneurosis which are alpha and beta-adrenergic antagonists.

BACKGROUND OF ART

A 1,4-benzodioxane derivative is used for an intermediate for the preparation of circulatory drugs and drugs for psychoneurosis having alpha and beta-adrenergic antagonist-activity and its various kind of processes are known. For example, a method of reacting a catechol derivative with glycidyl tosylate in the presence of sodium hydride (Japanese patent publication No.9613/1994) or a method of reacting a catechol derivative with epichlorohydrin in the presence of pyridine (J. Org. Chem. 46,3846 (1981)) is known. A method is also known to make a 1,4-benzodioxane skeleton by reactng a catechol derivative with glycerol 1-tosylate acetonide and, after removing the protective group, the acetonide, by introducing two tosyl groups onto it and then by isolating it, and further by cyclizing it (J. Chem. Soc., Chem. Commun., 921 (1976)).

Among the above methods, besides the method comprising the use of glycidyl tosylate is costly because of expense of that compound, the epoxy group is also reduced on the deprotection by hydrogenolysis and the yield decreases. In the method comprising the use of epichlorohydrin, the excess of epichlorohydrin and dichloropropanediol as a by-product must be eliminated by their evaporation with xylene, and the hydrochloric acid and acetic acid used must be eliminated by evaporation with ethanol, and therefore such procedures are troublesome. Moreover, the reaction is carried out under reflux of piperidine or hydrochloric acid. Therefore a compound having substituents which are unstable to an acid or a base can not be used. When using a optically active epichlorohydrin, racemization occurs and an optically pure product cannot be obtained. In the method which comprises the reaction of a catechol derivative with glycidyl 1-tosylate acetonide, the resulting ditosylated product must be separated after tosylation and therefore the yield of the ditosylated product is 55%, or lower. These methods have many disadvantages in application of an industrial scale. An improved method has been desired.

DISCLOSURE OF INVENTION

The present inventors, taking into consideration the above fact, extensively engaged in study to find an improved method for the preparation of a 1,4-benzodioxane derivative, and found the present invention. After sulfonating a phenoxypropanediol compound, by cyclizing the resulting product in the presence of a base, the desired 1,4-benzodioxane derivative is favorably obtained in an industrial scale.

The present invention relates to a process of preparing a 1,4-benzodioxane derivative as shown by the following formula (1)

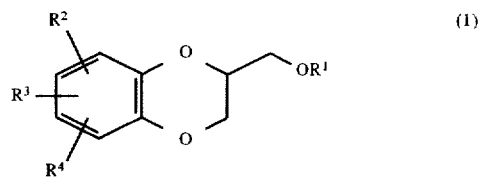

wherein $R^1$ is a hydrogen atom or $RSO_2$ in which R is $C_1$–$C_4$ alkyl, or phenyl which may be substituted by $C_1$–$C_4$ alkyl, $R^2$, $R^3$ and $R^4$ are, respectively, hydrogen, halogen, hydroxy, nitro, cyano, formyl, carboxyl, alkoxycarbonyloxy having 1–4 carbon atoms in the alkyl portion, $C_1$–$C_4$ alkyl, $C_1$–$C_4$ alkoxy, $C_1$–$C_4$ haloalkyl, N,N-di $C_1$–$C_4$ alkylamino, alkylcarbonyl having 1–4 carbon atoms in the alkyl portion, alkoxycarbonyl having 1–4 carbon atoms in the alkyl portion or phenyl which may be substituted by $C_1$–$C_4$ alkyl, or two groups among $R^2$, $R^3$, and $R^4$ may be combined together to constitute methylenedioxy on adjacent carbon atoms, or two groups among $R^2$, $R^3$ and $R^4$ may be combined together to constitute phenyl on the adjacent carbon atoms, which is characterized in reacting a diol compound as shown by the following formula (2)

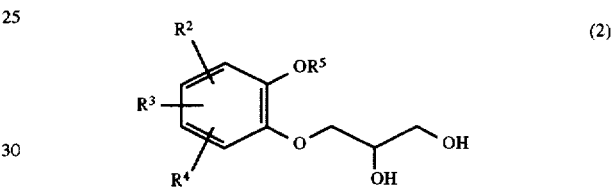

wherein $R^2$, $R^3$ and $R^4$ are the same as defined above. $R^5$ is benzyl, allyl (e.g. 2-propenyl, etc.), o-nitrobenzyl, t-butyldimethylsilyl or benzyloxycarbonyl, or $R^5$ may be constituted methylenedioxy, isopropylidenedioxy, cyclohexylidenedioxy or diphenylmethylenedioxy together with oxygen atom in the hydroxy or the $R^5O$-group, provided that when any one of $R^2$, $R^3$ and $R^4$ is hydroxy and the hydroxy is bound on the carbon atom adjacent to the carbon atom substituted by $R^5O$-group, with a sulfonyl halide in the presence of a base to give a sulfonated compound(s) as shown in the following formulae (3) and/or (4)

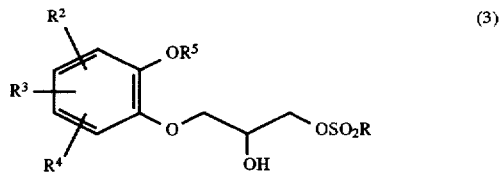

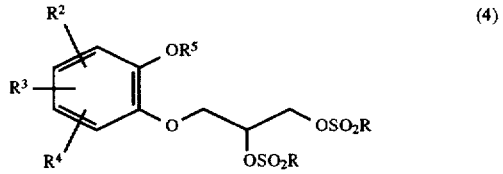

wherein R, $R^1$, $R^2$, $R^3$, $R^4$ and $R^5$ are the same as defined above, and after the elimination of the protective group $R^5$ of the sulfonated compound, cyclizing the compound by treating with a base.

BEST MODE OF PRESENT INVENTION

The present invention is described in detail as shown in the following reaction scheme.

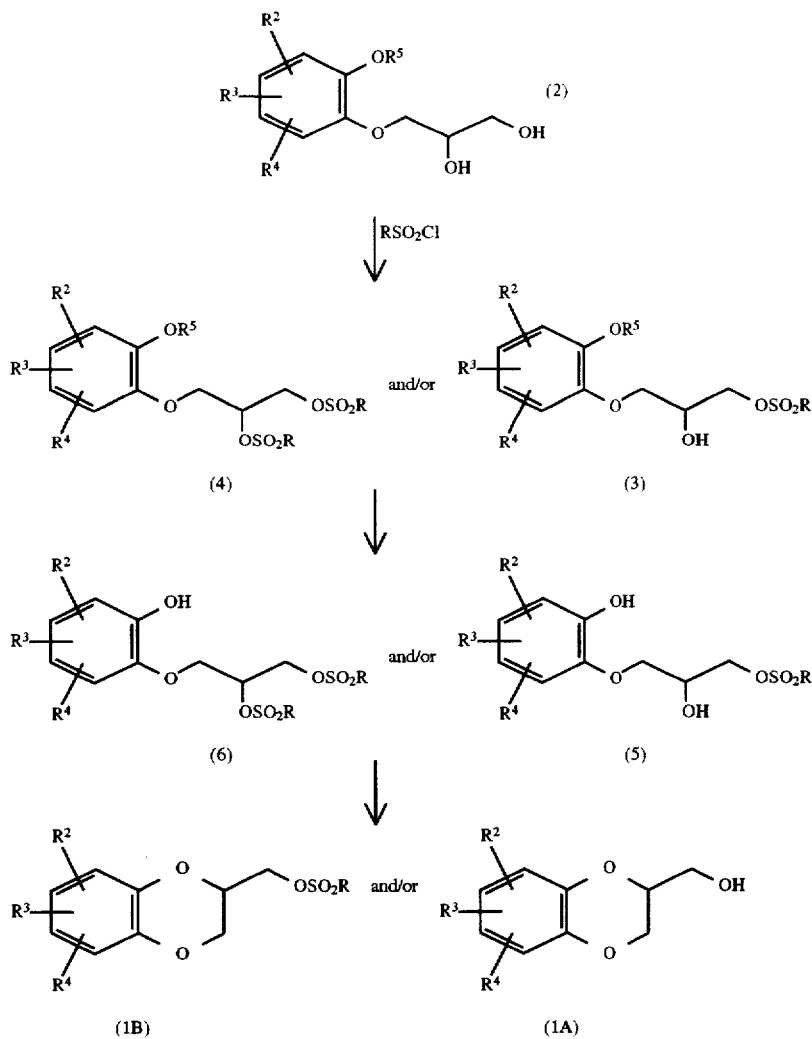

wherein R, $R^2$, $R^3$, $R^4$ and $R^5$ are the same as defined above.

First, a diol compound (2) is reacted with a sulfonyl halide for example, an arylsulfonyl halide, such as benzenesulfonyl chloride, toluenesulfonyl chloride, etc. or $C_1$–$C_4$ alkylsulfonyl halide, such as methanesulfonyl chloride, etc., in the presence of a base to give a monosulfonated compound (3) or a disulfonated compound (4) or a mixture of both compounds. As a base, an organic base, such as triethylamine, pyridine, etc., is used. This reaction is carried out in the absence of a solvent or in the presence of a solvent, for example, an ether, such as tetrahydrofuran, dioxane, t-butylmethyl ether, diethyl ether, etc., a chlorinated compound, such as methylene chloride, chloroform, dichloroethane, etc.; or an aromatic hydrocarbon, such as benzene, toluene, etc. The reaction temperature is 0°–100° C., preferably 10°–50° C. This reaction proceeds in the absence of a catalyst, and the reaction is accelerated by using N,N-dimethylaminopyridine, etc., as a catalyst, and the yield is improved. When a mixture of a monosulfonated compound (3) and a disulfonated compound (4) is produced, the mixture can be separated by liquid column chromatography, etc. But the mixture may be used without separation in the next step.

Next, the elimination of the protective group $R^5$ on the sulfonated compound (3) or (4) is carried out. When the protective group $R^5$ is benzyl, allyl or benzyloxycarbonyl, the protective group is deprotected by being subjected to catalytic hydrogenation with palladium-carbon at room temperature in an organic solvent, such as methanol, ethanol, ethyl acetate, etc. When an o-nitrobenzyl is used as a protective group, the group is eliminated by radiation on it in an organic solvent, such as methanol, ethanol, etc. When the protective group $R^5$ is t-butyldimethylsilyl, the protective group is removed by using a salt of a fluoro compound, such as sodium fluoride, potassium fluoride or tetrabutylammonium fluoride in an organic solvent, such as N,N-dimetylformamide, tetrahydrofuran, etc., or a mixture of the organic solvent and water. When the protective group $R^5$ is methylenedioxy, isopropylidenedioxy, cyclohexylidenedioxy or diphenylmethylenedioxy, the protective group is eliminated under acidic conditions usually used in the deprotection of such a protective group.

A compound (5), a compound (6) or a mixture of them thus obtained is cyclized by treating it with a base to produce a desired 1,4-benzodioxane derivative (1A) ($R^1$=H) and/or (1B) ($R^1$=$RSO_2$). Examples of the solvent are a dipolar aprotic solvent, such as N,N-dimethylformamide, dimethyl sulfoxide, sulfolane, hexamethylphosphoramide, etc.; an ether, such as tetrahydrofuran, dioxane, t-butylmethyl ether, diethyl ether, etc.; a chlorinated compound, such as methylene chloride, chloroform, dichloroethane, etc.; an alcohol, such as methanol, ethanol, isopropanol, t-butanol, etc.; water, and so on.

Examples of the base are an alkali metal hydride, an alkali metal hydroxide, an alkaline earth metal hydroxide, an alkali metal carbonate, an alkaline earth metal carbonate, an alkali metal salt of $C_1$–$C_4$ alkanol, or tri $C_1$–$C_4$ alkylamine. Sodium hydride, sodium hydroxide, potassium hydroxide, calcium hydroxide, sodium carbonate, potassium carbonate, sodium methoxide, sodium ethoxide, triethylamine and ethyldiisopropylamine are illustrated. The amount of the base is 1–5 mol, preferably 1–3 mol per compound (5) or (6). The reaction temperature is −20°–80° C., preferably 0°–50° C. It is thought that on the cyclization of a compound (5), an epoxide is produced and then the epoxide reacts with a hydroxy on the benzene ring to give the cyclized compound. In this reaction there is a possibility to produce a 6 membered ring and a 7 membered ring, but the 6 membered ring is preferentially produced.

A 1,4-benzodioxane derivative (1A) ($R^1$=H) thus prepared, is reacted with an arylsulfonyl halide, such as benzenesulfonyl chloride, toluenesulfonylchloride, etc.; or a $C_1$–$C_4$ alkylsulfonyl halide, such as methanesulfonyl chloride, etc., in the presence of a base to produce a 1,4-benzodioxane derivative (1B) ($R^1$ is $RSO_2$, R is $C_1$–$C_4$ alkyl, phenyl which may be substituted by $C_1$–$C_4$ alkyl). When a mixture of a compound (5) and a compound (6) is cyclized, a mixture of a 1,4-benzodioxane derivative (1) wherein $R^1$ is H, and a 1,4-benzodioxane derivative (1) wherein $R^1$ is $RSO_2$, is obtained, but this mixture is subjected to the next reaction with an arylsulfonyl halide or a $C_1$–$C_4$ alkylsulfonyl halide in the same method as mentioned above to give only a compound wherein $R^1$ is $RSO_2$.

A diol compound (2), a starting material of the present invention, is synthesized according to the reaction scheme as mentioned below.

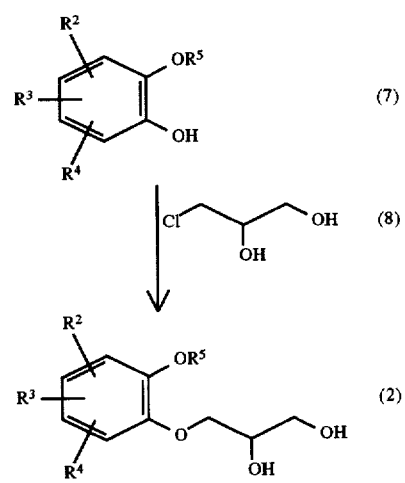

wherein $R^2$, $R^3$, $R^4$ and $R^5$ are the same as defined above.

That is, a catechol derivative (7) is reacted with 3-chloro-1,2-propanediol (8) in the presence of a base in a solvent to produce a diol compound (2). The solvent is a dipolar aprotic solvent, such as N,N-dimethylformamide, dimethyl sulfoxide, sulfolane, hexamethylphosphoramide, etc.; an ether, such as tetrahhdrofuran, dioxane, t-butylmethyl ether, diethyl ether, etc.; a chlorinated compound, such as methylene chloride, chloroform, dichloroethane, etc.; an alcohol, such as methanol, ethanol, isopropanol, t-butanol, etc.; water, and so on.

Examples of the base are an alkali metal hydride, an alkali metal hydroxide, an alkaline earth metal hydroxide, an alkali metal carbonate, an alkaline earth metal carbonate, an alkali metal salt of $C_1$–$C_4$ alkanol, or tri $C_1$–$C_4$ alkylamine. Sodium hydride, sodium hydroxide, potassium hydroxide, calcium hydroxide, sodium carbonate, potassium carbonate, sodium methoxide, sodium ethoxide, triethylamine and ethyldiisopropylamine are illustrated. Sodium hydride, sodium methoxide or sodium ethoxide is preferably used, and sodium hydride among them is more preferably used. The amount of the base is 1–4 mol, preferably 1.1–2.5 mol per compound (7). The reaction temperature is −20°–150° C., preferably 20°–100° C. When the reaction temperature is too low, the reaction rate decreases and that is not practical. On the other hand, when the temperature is too high, a glycidol produced during the reaction may be polymerized and the yield is significantly reduced.

A diol compound (2), a starting material, used in the present invention, may be prepared by the known method, that is by reacting a catechol derivative (7) with glycidol. Glycidol is unstable and is readily polymerized, but 3-chloro-1,2-propanediol (8) is stable and not expensive and the method consisting of the use of this compound (8) as mentioned above, therefore, is beneficial in the industrial scale.

Also, by using an optically active diol compound (2), an optically active 1,4-benzodioxane derivative is prepared. Such an optically active diol compound (2) is prepared, for instance, by reacting a catechol derivative (7) with optically active 3-chloro-1,2-propanediol under the same conditions mentioned above. When 3-chloro-1,2-propanediol having high optical purity is used as a starting material, the racemization is not markedly occurred during the reaction and therefore, a 1,4-benzodioxane derivative is obtainable in the high optical purity. 3-Chloro-1,2-propanediol having the high optical purity (more than 98% ee), for example, is obtained by using the method described in Japanese patent publication No.73998/1992 or No.73999/1992 developed by the present applicant. According to the process of the present invention, a (S)-1,4-benzodioxane derivative is obtained from (R)-3-chloro-1,2-propanediol, and a (R)-1,4-benzodioxane derivative is obtained from (S)-3-chloro-1,2-propanediol.

The present invention is in detail explained in the following Examples, but the invention is not limited to the examples.

EXAMPLE 1

(i) Preparation of a Diol Compound

Sodium hydride (2.07 g, 0.05 mol in oil (60% w/w)) was washed with n-hexane, and anhydrous N,N-dimethylformamide (15 ml) was added to it. To the suspension was dropped 2-benzyloxyphenol (6 g, 0.03 mol) in anhydrous N,N-dimethylformamide (10 ml) under ice cooling in over a 10 minute period. After the emission of gas was over, to the solution was dropped monochlorohydrin (3.98 g, 0.036 mol) in anhydrous N,N-dimethylformamide (5 ml) under ice cooling. The solution was stirred for 3 hours at 60° C. After the reaction was completed, to the reaction mixture was added a saturated aqueous solution of ammonium chloride (500 ml) and the mixture was extracted with ethyl acetate, and the ethyl acetate phase was washed with saturated brine and water, dried over anhydrous magnesium sulfate and concentrated in vacuo to give a crude product as a pale yellow oil. The crude product was purified with column chromatography (silica gel, n-hexane/ethyl acetate (6:1)) to give 3-(2-benzyloxy)phenoxy-1,2-propanediol (7.88 g) as a colorless oil.

(ii) Preparation of a Compound (3) and a Compound (4)

The diol compound (7.88 g, 0.029 mol) obtained above (i) was dissolved in pyridine (10 ml) and to the solution was added p-toluenesulfonyl chloride (12.16 g, 0.064 mol) under ice cooling and then the mixture was stirred at room temperature for 12 hours. After the reaction was over, to the reaction mixture was added a 3% aqueous solution of hydrochloric acid (300 ml) and the mixture was extracted with ethyl acetate. The ethyl acetate phase was washed twice with water, dried over anhydrous magnesium sulfate and concentrated in vacuo to give 15.2 g of a mixture of a ditosylated compound and a monotosylated compound (ratio,6:1) as a pale yellow oil.

(iii) Preparation of a Compound (5) and a Compound (6)

In a mixture of ethanol (600 ml) and ethyl acetate (100 ml) was dissolved 15.2 g of a mixture of a ditosylated compound and a monosylated compound prepared above (ii) and the solution was subjected to hydrogenation under hydrogen in the presence of 10% palladium on carbon (1 g). After the reaction was finished, palladium/carbon was filtered off and the filtrate was concentrated in vacuo to give 12.9 g of a mixture of 1,2-ditosylated 3-(2-hydroxyphenoxy)-1,2-propanediol and 1-monotosylated 3-(2-hydroxyphenoxy)-1,2-propanediol.

(iv) Preparation of a 2,3-Dihydro-1,4-Benzodioxane Derivative

Sodium hydride (1.59 g, 0.04 mol in oil (60% w/w)) was washed with n-hexane and to it was added 10 ml of anhydrous N,N-dimethylformamide. To the suspension was added 12.9 g of a mixture of a 1,2-ditosylated compound and a 1-tosylated compound prepared above (iii) in anhydrous N,N-dimethylformamide (100 ml) under an atmosphere of nitrogen under ice cooling in over a 10 minute period and then the mixture was stirred for 3 hours at room temperature. To the solution was added a saturated aqueous solution of ammonium chloride and the solution was extracted with ethyl acetate. The ethyl acetate phase was washed with saturated brine and water, dried over anhydrous magnesium sulfate and concentrated in vacuo to give 7.5 g of a crude mixture of 2-tosyloxymethyl-1,4-benzodioxane and 2-hydroxymethyl-1,4-benzodioxane as a oil. The mixture might be purified with column chromatography (silica gel, n-hexane/ethyl acetate (3:2)), but the mixture was used for the next step without purification.

To 7.5 g of the mixture of 2-tosyloxymethyl-1,4-benzodioxane and 2-hydroxymethyl-1,4-benzodioxane in dichloromethane (15 ml) and pyridine (3.16 g, 0.04 mol) was added p-toluenesulfonyl chloride (0.76 g, 0.04 mol) under ice cooling and the mixture was stirred at room temperature for 12 hours. After the completion of the reaction, a 3% aqueous solution of hydrochloric acid (200 ml) was added to the reaction mixture and the reaction mixture was extracted with ethyl acetate and the ethyl acetate phase was washed twice with water, dried over anhydrous magnesium sulfate, and concentrated in vacuo to give a crude product as a oil. The crude product was purified with column chromatography (silica gel, n-hexane/ethyl acetate (3:1)) to give 7.89 g of 2-tosyloxymethyl-1,4-benzodioxane (yield 83% : based on 2-benzyloxyphenol).

EXAMPLE 2

By using 2-benzyloxy-3-methylphenol (6.43 g) instead of 2-benzyloxyphenol and by using optically active (R)-monochlorohydrin (optical purity:99.0% ee), according to the method of example 1 there was obtained (S)-2-tosyloxymethyl-8-methyl-1,4-benzodioxane (8.02 g, yield 80%). During the reaction the optical purity of (S)-2-hydroxymethyl-8-methyl-1,4-benzodioxane was 97.4% ee by the measurement with the chiral column OD (Daisel Chemical Industries Ltd.)

EXAMPLE 3

By using 2-benzyloxy-4,5-methylenedioxyphenol (7.33 g) instead of 2-benzyloxyphenol in the same method described in Example 1, there was obtained 2-tosyloxymethyl-6,7-methylenedioxy-1,4-benzodioxane (8.5 g, yield 78%).

EXAMPLE 4

By using 2-benzyloxy-3-methoxyphenol (6.91 g) instead of 2-benzyloxyphenol in the same method described in Example 1, there was obtained 2-tosyloxymethyl-8-methoxy-1,4-benzodioxane (8.51 g, yield 81%).

EXAMPLE 5

By using 2-benzyloxy-6-fluorophenol (6.55 g) instead of 2-benzyloxyphenol in the same method described in Example 1, there was obtained 2-tosyloxymethyl-5-fluoro-1,4-benzodioxane (7.04 g, yield 69%).

EXAMPLE 6

By using 2-benzyloxy-5-nitrophenol (7.36 g) instead of 2-benzyloxyphenol in the same method described in Example 1, there was obtained 2-tosyloxymethyl-6-nitro-1,4-benzodioxane (7.92 g, yield 72%).

EXAMPLE 7

By using 2-benzyloxy-5-ethoxycarbonylphenol (8.17 g) instead of 2-benzyloxyphenol in the same method described in Example 1, there was obtained 2-tosyloxymethyl-7-ethoxycarbonyl-1,4-benzodioxane (8.85 g, yield 75%).

EXAMPLE 8

On the occasion of the preparation of 2-tosyloxymethyl-8-hydroxy-1,4-benzodioxane, by using 4-hydroxy-2,2-dimethyl-1,3-benzo[d]dioxole (4.98 g) instead of 2-benzyloxyphenol, the objective compound was obtained, according to the method described in Example 1, provided that, intermediates (5) and (6) wherein R is p-$CH_3C_6H_4$, $R^2$ is 3-OH, $R^3$ and $R^4$ are H, were prepared as the following procedure.

A mixture (14.3 g) of a compound (3) and a compound (4) wherein R is p-$CH_3C_6H_4$, $R^2$ and R5 are -OC($CH_3$)$_2$-, $R^3$ and $R^4$ are hydrogen, was refluxed in 6N hydrochloric acid for 4 hours. After the reaction was over, to the mixture is added methylene chloride and the methylene chloride phase was washed with a saturated aqueous solution of sodium hydrogen carbonate and water, dried over anhydrous magnesium sulfate and concentrated in vacuo to give 11.8 g of a mixture of a compound (5) and a compound (6).

This mixture was treated in the same method described in Example 1 to give the objective compound (6.55 g, yield 65%).

EFFECT OF INVENTION

According to the present invention, a 1,4-benzodioxane derivative is prepared in the high yield and by the convenient procedures in the industrial scale without the isolation of the intermediate produced during the reaction, by using a diol compound which is synthesized from a catechol derivative. Especially, it is economical to prepare a diol compound by reacting a catechol derivative with 3-chloro-1,2-propanediol. And in this reaction, by using an optically active 3-chloro-1,2-propanediol, a 1,4-benzodioxane of high optical purity is obtainable without marked racemizaion during the reaction.

We claim:

1. A process for preparing a 1,4-benzodioxane derivative as shown by the following formula (1)

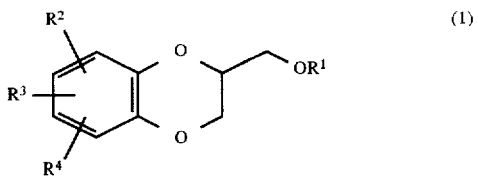

(1)

wherein $R^1$ is hydrogen atom or $RSO_2$ in which R is $C_1$–$C_4$ alkyl, or phenyl which may be substituted by $C_1$–$C_4$ alkyl, $R^2$, $R^3$ and $R^4$ are respectively hydrogen, halogen, hydroxy, nitro, cyano, formyl, carboxyl, alkoxycarbonyloxy having 1–4 carbon atoms in the alkyl portion, $C_1$–$C_4$ alkyl, $C_1$–$C_4$ alkoxy, $C_1$–$C_4$ haloalkyl, N,N-di $C_1$–$C_4$ alkylamino, alkylcarbonyl having 1–4 carbon atoms in the alkyl portion, alkoxycarbonyl having 1–4 carbon atoms in the alkyl portion or phenyl which may be substituted by $C_1$–$C_4$ alkyl, or two groups among $R^2$, $R^3$, and $R^4$ may be combined together to constitute methylenedioxy on adjacent carbon atoms, or two groups among $R^2$, $R^3$ and $R^4$ may be combined together to constitute phenyl on adjacent carbon atoms, wherein a diol compound as shown by the following formula (2)

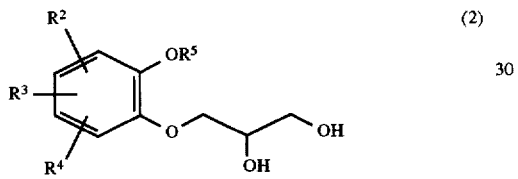

(2)

wherein $R^2$, $R^3$ and $R^4$ are same as defined above, $R^5$ is benzyl, allyl, o-nitrobenzyl, t-butyldimethylsilyl or benzyloxycarbonyl, or $R^5$ may be constituted methylenedioxy, isopropylidenedioxy, cyclohexylidenedioxy or diphenylmethylenedioxy together with oxygen atom in the hydroxy or the $R^5$O-group, provided that when any one of $R^2$, $R^3$ and $R^4$ is hydroxy and the hydroxy is bound on the carbon atom adjacent to the carbon atom substituted by $R^5$O-group, is reacted with a sulfonyl halide in the presence of a base to obtain a sulfonated compound as shown by the following formulae (3) and/or (4)

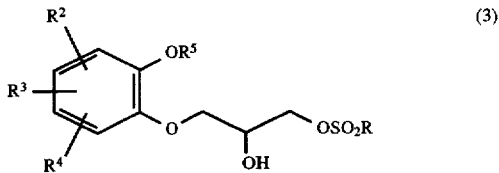

(3)

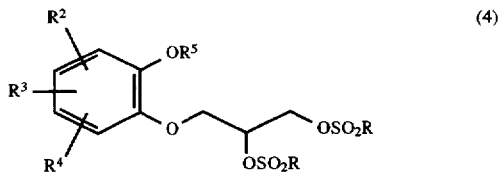

(4)

wherein R, $R^1$, $R^2$, $R^3$, $R^4$, and $R^5$ are the same as defined above, and after elimination of the protective group $R^5$ of the sulfonated compound, the compound is cyclized by treating with a base.

2. The process for preparing a 1,4-benzodioxane derivative claimed in claim 1 wherein, after the elimination of the protective group on a mixture of a compound shown by the formula (3) and a compound shown by the formula (4), the deprotected compound is subjected to cyclization under a base, and the cyclized compound shown by the formula (1) is further reacted with a sulfonyl halide.

3. The process for preparing a 1,4-benzodioxane derivative claimed in claim 1 wherein an optically active 1,4-benzodioxane derivative is prepared by using an optically active diol shown in formula (2).

4. The process for preparing a 1,4-benzodioxane derivative claimed in claim 1 wherein the sulfonyl halide is toluenesulfonyl chloride or $C^1$–$C^4$ alkyl sulfonyl chloride.

5. The process for preparing a 1,4-benzodioxane derivative claimed in claim 4 wherein the sulfonyl halide is toluenesulfonyl chloride.

6. The process for preparing a 1,4-benzodioxane derivative claimed in claim 1 in which the protective group $R^5$, wherein $R^5$ is benzyl, allyl or benzyloxycarbonyl, on the sulfonated compound shown by formula (3) or (4) is eliminated under hydrogenation with palladium/carbon in an organic solvent.

7. The process for preparing a 1,4-benzodioxane derivative claimed in claim 1 wherein a catechol derivative shown by the following formula (7)

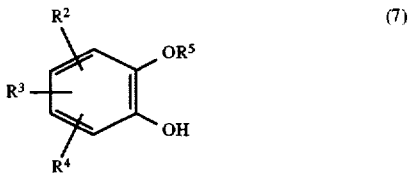

(7)

wherein $R_2$, $R^3$, $R^4$ and $R^5$ are the same defined in claim 1, is reacted with 3-chloro-1,2-propanediol shown by the following formula (8)

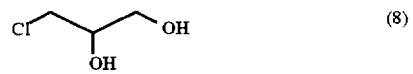

(8)

in the presence of a base to obtain a diol compound shown by the formula (2).

8. The process for preparing an optically active 1,4-benzodioxane derivative claimed in claim 3 wherein a catechol derivative shown by the following formula (7)

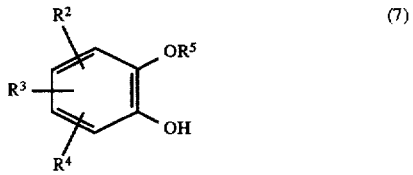

(7)

wherein $R^2$, $R^3$, $R^4$ and $R^5$ are the same defined above, is reacted with an optically active 3-chloro-1,2-propanediol shown by the following formula (8)

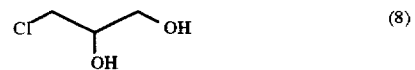

(8)

in the presence of a base to obtain the optically active diol compound shown by the formula (2).

* * * * *

UNITED STATES PATENT AND TRADEMARK OFFICE
CERTIFICATE OF CORRECTION

PATENT NO. : 5,780,650
DATED : July 14, 1998
INVENTOR(S) : Furukawa et al

It is certified that error appears in the above-identified patent and that said Letters Patent is hereby corrected as shown below:

On the title page: Item [56] insert the following:

FOREIGN PATENT DOCUMENTS

| | | DOCUMENT NUMBER | | | | | | PUBLICATION DATE | COUNTRY OR PATENT OFFICE | CLASS | SUBCLASS | TRANSLATION YES | NO |
|---|---|---|---|---|---|---|---|---|---|---|---|---|---|
| | | 0 | 5 | 6 | 5 | 7 | 32 | A1 | 4/93 | EP | | | | |

OTHER DOCUMENTS

| | | |
|---|---|---|
| | Willard et al., "Potential Diuretic-β-Adrenergic Blocking Agents: Synthesis of 3-[2-[(1,1-Dimethylethyl)amino]-1-hydroxyethyl]-1,4-dioxino[2,3-g]quinolines", *J. Org. Chem*, 1981, 46, 3846-3852 | |
| | Nelson et al., "Absolute Configuration of 2-Alkylaminomethylbenzodioxans, Competitive α-Adrenergic Antagonists", *J.C.S. Chem. Comm.*, 1976, pp. 921-922 | |
| | Marciniak et al., "New 1,4-Dihydropyridine Derivatives Combining Calcium Antagonism and α-Adrenolytic Properties", *J. Med. Chem.*, 1989, 32, 1402-1407 | |
| | FERRI et al., "Synthesis, Binding Affinities For a-Adrenoceptor and Eudismic Analysis of Chiral Benzodioxane Derivatives and Their Chiral Opened Analogues, Il Farmaco, Supplemental No. 12, 1998 | |

Signed and Sealed this

Fourth Day of May, 1999

Attest:

Q. TODD DICKINSON

*Attesting Officer*    *Acting Commissioner of Patents and Trademarks*